(12) United States Patent
Huh et al.

(10) Patent No.: US 9,392,934 B2
(45) Date of Patent: Jul. 19, 2016

(54) PROBE FOR DIAGNOSING OTITIS MEDIA USING TERAHERTZ WAVES AND OTITIS MEDIA DIAGNOSIS SYSTEM AND METHOD

(71) Applicant: Industry-Academic Cooperation Foundation, Yonsei University, Seoul (KR)

(72) Inventors: Yong-Min Huh, Seoul (KR); Jin-Suck Suh, Seoul (KR); Seung-Jae Oh, Gwangmyeong-si (KR); Joo-Hiuk Son, Seoul (KR); Tae-In Jeon, Busan (KR); Jae Young Choi, Seoul (KR); Hyun Yong Choi, Seoul (KR); Sang-Hoon Kim, Seongnam-si (KR); Ki Young Jeong, Seoul (KR); Young Bin Ji, Busan (KR)

(73) Assignee: Industry-Academic Cooperation Foundation, Yonsei University, Seoul (KR)

( * ) Notice: Subject to any disclaimer, the term of this patent is extended or adjusted under 35 U.S.C. 154(b) by 23 days.

(21) Appl. No.: 14/355,328

(22) PCT Filed: Nov. 2, 2012

(86) PCT No.: PCT/KR2012/009187
§ 371 (c)(1),
(2) Date: Apr. 30, 2014

(87) PCT Pub. No.: WO2013/066107
PCT Pub. Date: May 10, 2013

(65) Prior Publication Data
US 2014/0249426 A1    Sep. 4, 2014

(30) Foreign Application Priority Data
Nov. 2, 2011  (KR) .................. 10-2011-0113268

(51) Int. Cl.
A61B 1/227 (2006.01)
A61B 5/05 (2006.01)
A61B 5/053 (2006.01)

(52) U.S. Cl.
CPC ............... *A61B 1/227* (2013.01); *A61B 5/0507* (2013.01); *A61B 5/0536* (2013.01)

(58) Field of Classification Search
CPC ..... A61B 1/227; A61B 5/0507; A61B 5/0536
See application file for complete search history.

(56) References Cited

U.S. PATENT DOCUMENTS

2003/0023284 A1* 1/2003 Gartstein et al. ................ 607/88
2006/0167531 A1* 7/2006 Gertner et al. .................. 607/86

(Continued)

FOREIGN PATENT DOCUMENTS

KR 20090098458 A 9/2009
KR 100945280 B1 2/2010

(Continued)

*Primary Examiner* — Baisakhi Roy
(74) *Attorney, Agent, or Firm* — The Webb Law Firm

(57) ABSTRACT

The present invention relates to a otitis media diagnosis system using terahertz electromagnetic waves, which can diagnose otitis media using terahertz electromagnetic waves in a non-invasive manner, and which can accurately diagnose otitis media by acquiring images on the tympanic cavity using terahertz electromagnetic waves with excellent transmittance, and which can quickly and accurately divide exudative otitis media and suppurative otitis media using terahertz electromagnetic waves that are sensitive to moisture, and which is safe to a body using terahertz electromagnetic waves. The otitis media diagnosis system includes a terahertz probe including a generating unit for radiating terahertz electromagnetic waves from the outside of an ear toward a tympanic cavity and a detection unit for detecting the reflected terahertz electromagnetic waves reflected from the tympanic cavity.

11 Claims, 4 Drawing Sheets

(56) References Cited

U.S. PATENT DOCUMENTS

| | | | |
|---|---|---|---|
| 2006/0217612 A1* | 9/2006 | Ouchi | 600/407 |
| 2006/0278245 A1* | 12/2006 | Gan | 128/898 |
| 2007/0129632 A1* | 6/2007 | Voie et al. | 600/438 |
| 2008/0237028 A1* | 10/2008 | Kislev | 204/157.15 |
| 2009/0185191 A1* | 7/2009 | Boppart et al. | 356/479 |
| 2009/0287091 A1 | 11/2009 | Son et al. | |
| 2009/0290149 A1* | 11/2009 | Roth | 356/300 |
| 2011/0184654 A1* | 7/2011 | Ben-David et al. | 702/19 |
| 2013/0046357 A1* | 2/2013 | Neev | 607/45 |
| 2013/0289353 A1* | 10/2013 | Seth et al. | 600/200 |

FOREIGN PATENT DOCUMENTS

| | | |
|---|---|---|
| KR | 20100130765 A | 12/2010 |
| KR | 101009779 B1 | 1/2011 |
| KR | 101065496 B1 | 9/2011 |

* cited by examiner

PROBE FOR DIAGNOSING OTITIS MEDIA USING TERAHERTZ WAVES AND OTITIS MEDIA DIAGNOSIS SYSTEM AND METHOD

CROSS-REFERENCE TO RELATED APPLICATIONS

This application is the U.S. national phase of International Application No. PCT/KR2012/009187 filed Nov. 2, 2012, and claims priority to Korean Patent Application No. 10-2011-0113268 filed Nov. 2, 2011, the disclosures of which are hereby incorporated in their entirety by reference.

BACKGROUND OF THE INVENTION

1. Field of the Invention

The present invention relates to a probe for diagnosing otitis media using terahertz electromagnetic waves, and system and method for diagnosing otitis media using the same, which can diagnose occurrence, kinds, progression, and state of otitis media using terahertz electromagnetic waves.

2. Background of the Related Art

Otitis media is inflammation of the tympanic cavity, occurs at a wide age group, from infants to adults, and is a common disease that about 30 percent of infants under the age of three have at least three times. According to clinical signs, otitis media is divided into acute otitis media and exudative otitis media, and is classified into chronic otitis media when otitis media symptoms are continued longer than three months.

Symptoms of acute otitis media are earache, fever, flare of the eardrum, expansion, impaired motility, and suppurative secretion. Moreover, because acute otitis media frequently recurs, a patient must be medicated antibiotics for several months while observing improvement of the symptoms. On the contrary, exudative otitis media has an exudation in the tympanic cavity without any symptoms of acute infections, such as earache, fever or others, and hence, is treated by different methods without medication of antibiotics differently from acute otitis media. Therefore, acute otitis media and exudative otitis media must be exactly divided and treated by curing methods that are right for the symptoms. Furthermore, it is important to correctly diagnose because otitis media frequently recurs and causes serious complications if the treatment is failed, but the doctor cannot provide correct and safe diagnosis and it is very difficult to correctly diagnose because otitis media occurs at the back of the eardrum.

As methods for diagnosing otitis media, there are a direct clinical examination method (otoscopy), a diagnostic suspicion of otitis media through an opinion on the eardrum, a hearing test using an impedance audiometer for generating a sound to measure an echo sound, and a method for directly perforating the eardrum using a syringe to examine the eardrum.

However, the direct examination has a great possibility of misdiagnosis of acute otitis media and exudative otitis media, and hence, it may cause complications due to abuse of antibiotics and inappropriate treatment. The hearing test using the impedance audiometer is complicated in measurement and causes many errors according to patients' age or gender. Additionally, the method for directly perforating the eardrum may cause side effects due to perforation and causes an intense pain, and cannot be applied to infants who occupy most of the patients having a middle ear infection.

Korean Patent Laid-open No. 10-2010-130,765 discloses a probe for diagnosing exudative otitis media, which can diagnose occurrence of exudative otitis media using the characteristic that there are different forms of reflected waves of ultrasonic waves according to whether or not there is any exudation which is higher in viscosity than a carrier after injecting the carrier, such as distilled water, into the external auditory meatus. However, the conventional diagnosis probe has a disadvantage in that it is difficult to give a right prescription to the patient because it is difficult to diagnose suppurative otitis media or acute otitis media and to grasp progression of the disease. Moreover, the conventional diagnosis probe has further disadvantages in that it is difficult to diagnosis the disease at the early stage in the case that reflected waves of ultrasonic waves are used, and in that it is difficult to remove the carrier after diagnosis due to the viscosity of the carrier injected into the external auditory meatus.

SUMMARY OF THE INVENTION

Accordingly, the present invention has been made in view of the above-mentioned problems occurring in the prior art, and it is an object of the present invention to provide a probe for diagnosing otitis media using terahertz electromagnetic wave, and system and method for diagnosing otitis media using the same, which can diagnose otitis media using terahertz electromagnetic waves in a non-invasive manner.

It is another object of the present invention to provide a probe for diagnosing otitis media using terahertz electromagnetic wave, and system and method for diagnosing otitis media using the same, which can accurately diagnose otitis media by acquiring images on the tympanic cavity using terahertz electromagnetic waves with excellent transmittance.

It is a further object of the present invention to provide a probe for diagnosing otitis media using terahertz electromagnetic wave, and system and method for diagnosing otitis media using the same, which can quickly and accurately divide exudative otitis media and suppurative otitis media using terahertz electromagnetic waves that are sensitive to moisture.

It is a still further object of the present invention to provide a probe for diagnosing otitis media using terahertz electromagnetic wave, and system and method for diagnosing otitis media using the same, which use terahertz electromagnetic waves which is safe to a body.

It is another object of the present invention to provide a probe for diagnosing otitis media using terahertz electromagnetic wave, and system and method for diagnosing otitis media using the same, which do not cause scattering in the ear and do not need any carrier due to a strong straightness.

It is a further object of the present invention to provide a probe for diagnosing otitis media using terahertz electromagnetic wave, and system and method for diagnosing otitis media using the same, which can diagnose the disease at the early stage by recognizing moisture generated at the early stage of otitis media using characteristics of terahertz electromagnetic waves that are sensitive to moisture.

To accomplish the above object, according to the present invention, there is provided a probe for diagnosing otitis media including: an otoscope inserted into an inner ear; a generating unit for radiating terahertz electromagnetic waves from the outside of an ear toward a tympanic cavity through the otoscope; and a detection unit for detecting the reflected terahertz electromagnetic waves reflected from the tympanic cavity.

The generating unit radiates terahertz electromagnetic waves ranging from 0.01 THz to 30 THz.

The generating unit radiates at least ones of pulse type terahertz electromagnetic waves, continued-type terahertz electromagnetic waves, and semiconductor device type terahertz electromagnetic waves.

The probe further includes a camera for acquiring image information of the inner ear.

In another aspect of the present invention, the present invention provides a system for diagnosing otitis media using terahertz electromagnetic waves including: a terahertz probe which includes a generating unit for radiating terahertz electromagnetic waves from the outside of an ear toward a tympanic cavity and a detection unit for detecting the reflected terahertz electromagnetic waves reflected from the tympanic cavity; a converting unit which converts the reflected terahertz electromagnetic waves detected by the detection unit into an electrical signal and sends the electrical signal to a control unit; and a control unit which performs otitis media diagnosis using the electrical signal sent from the converting unit.

The generating unit radiates terahertz electromagnetic waves ranging from 0.01 THz to 30 THz.

The generating unit radiates at least ones of pulse type terahertz electromagnetic waves, continued-type terahertz electromagnetic waves, and semiconductor device type terahertz electromagnetic waves.

The control unit generates an image using the electric signal.

The control unit diagnoses otitis media by analyzing the image generated using the electric signal.

The otitis media diagnosing system further includes a display unit for displaying the image generated from the control unit.

The otitis media diagnosing system further includes a storage unit for storing the image generated from the control unit.

The converting unit amplifies a signal of the reflected terahertz electromagnetic waves and removes noise contained in the reflected terahertz electromagnetic waves.

The terahertz probe further comprises a camera for acquiring image information of the inner ear.

The terahertz probe further comprises an otoscope which is inserted into the inner ear.

The control unit diagnoses otitis media by discriminating occurrence, progression or kinds of otitis media.

In another aspect of the present invention, the present invention provides a method for diagnosing otitis media using terahertz electromagnetic waves including: a first step of radiating terahertz electromagnetic waves from the outside of an ear toward the tympanic cavity by a generating unit; a second step of detecting terahertz electromagnetic waves reflected from the tympanic cavity by a detection unit; a third step of converting the reflected terahertz electromagnetic waves into an electric signal and transferring the electric signal to a control unit by a converting unit; and a fourth step of analyzing a wavelength strength of the electric signal and diagnosing whether exudative otitis media or suppurative otitis media occurs by the control unit.

The third step further comprises a step of amplifying the reflected terahertz electromagnetic waves and removing noise contained in the reflected terahertz electromagnetic waves by the converting unit.

In the fourth step, the control unit diagnoses otitis media through wavelength strength of the electric signal received from the converting unit or through a spectrum analysis.

The otitis media diagnosing method further includes the steps of: creating an image using the electric signal received from the converting unit and transferring the image to a display unit by the control unit; and displaying the image by the display unit.

The otitis media diagnosing method further includes the step of analyzing the image to diagnose otitis media by the control unit.

According to the preferred embodiments of the present invention, the probe for diagnosing otitis media using terahertz electromagnetic wave, and system and method for diagnosing otitis media using the same can diagnose otitis media using terahertz electromagnetic waves in a non-invasive manner.

The probe for diagnosing otitis media using terahertz electromagnetic wave, and system and method for diagnosing otitis media using the same can accurately diagnose otitis media by acquiring images on the tympanic cavity using terahertz electromagnetic waves with excellent transmittance.

The probe for diagnosing otitis media using terahertz electromagnetic wave, and system and method for diagnosing otitis media using the same can quickly and accurately divide exudative otitis media and suppurative otitis media using terahertz electromagnetic waves that are sensitive to moisture.

The probe for diagnosing otitis media using terahertz electromagnetic wave, and system and method for diagnosing otitis media using the same use terahertz electromagnetic waves which is safe to a body.

The probe for diagnosing otitis media using terahertz electromagnetic wave, and system and method for diagnosing otitis media using the same do not cause scattering in the ear and do not need any carrier due to a strong straightness.

The probe for diagnosing otitis media using terahertz electromagnetic wave, and system and method for diagnosing otitis media using the same can diagnose the disease at the early stage by recognizing moisture generated at the early stage of otitis media using characteristics of terahertz electromagnetic waves that are sensitive to moisture.

BRIEF DESCRIPTION OF THE DRAWINGS

The above and other objects, features and advantages of the present invention will be apparent from the following detailed description of the preferred embodiments of the invention in conjunction with the accompanying drawings, in which.

DETAILED DESCRIPTION OF THE PREFERRED EMBODIMENT

Figure 1:
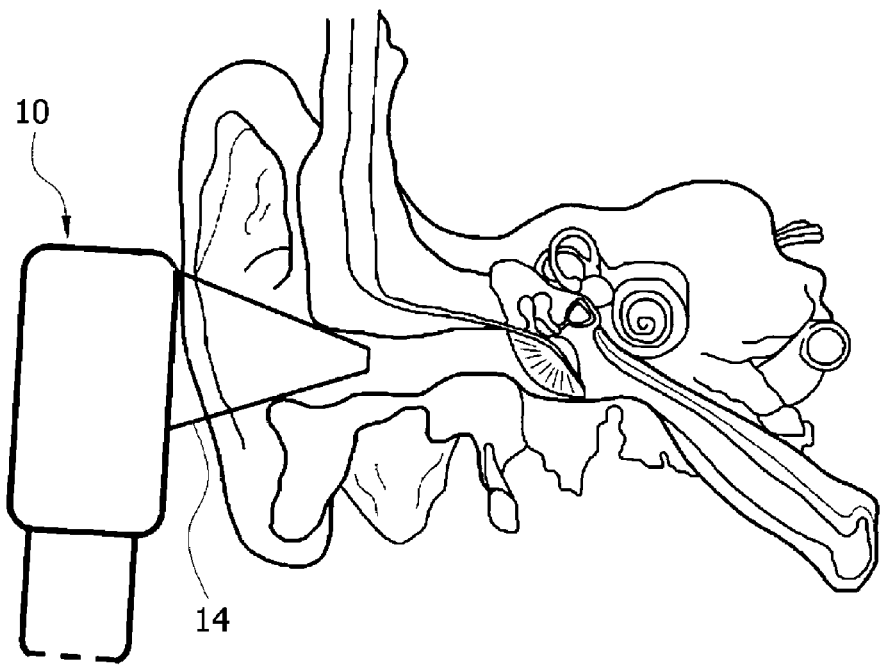
FIG. 1 is a view showing a terahertz probe and the inner ear structure according to a preferred embodiment of the present invention.

Hereinafter, reference will be now made in detail to the preferred embodiments of the present invention with reference to the attached drawings. In the drawings, the same components have the same reference numerals even though they are illustrated in different figures. In addition, in the description of the present invention, when it is judged that detailed descriptions of known functions or structures related with the present invention may make the essential points vague, the detailed descriptions of the known functions or structures will be omitted.

FIG. 1 is a view showing a terahertz probe and the inner ear structure according to a preferred embodiment of the present invention.

The terahertz probe 10 according to the preferred embodiment of the present invention includes: a generating unit 11 for radiating terahertz electromagnetic waves from the outside of an ear toward a tympanic cavity; a detection unit for detecting the reflected terahertz electromagnetic waves reflected from the tympanic cavity; a camera 13 for acquiring image information of the inner ear; and an otoscope 14 inserted into the inner ear.

The generating unit 11 includes: a generating part (not shown) for generating terahertz electromagnetic waves; a transferring part (not shown) for transferring the generated terahertz electromagnetic waves to the otoscope 14; and a radiating part (not shown) for radiating the transferred terahertz electromagnetic waves to the tympanic cavity through the otoscope 14. The generating part can generate terahertz electromagnetic waves ranging from 0.01 THz to 30 THz. The transferring part serves to transfer the generated terahertz electromagnetic waves to the radiating part, and is made of optical fiber. The radiating part radiates terahertz electromagnetic waves excited from the generating part toward the tympanic cavity, and in this instance, the radiated terahertz electromagnetic waves reach the tympanic cavity after penetrating the eardrum due to its penetrability. The generating unit 11 generates at least ones of pulse type terahertz electromagnetic waves, continued-type terahertz electromagnetic waves, and semiconductor device type terahertz electromagnetic waves, and then, radiates them toward the tympanic cavity. The pulse type terahertz electromagnetic waves can be generated through one of technologies using a photoconductive antenna using a femtosecond laser, optical rectification, and conductor electrical surface field. The continued-type terahertz electromagnetic waves can be generated using a vacuum electron device and a free electron laser based on vacuum electron beams, a photomixer based on a laser, a gas laser or a TPO (THz Parametric Oscillator, and the semiconductor device type terahertz electromagnetic waves can be generated using a quantum cascade laser based on a semiconductor. Out of them, the vacuum electron device is small in thermal loss and is relatively high in energy conversion efficiency because using vacuum electron beams, and hence, is appropriate to small-sized high-power terahertz elements like the present invention in the case of grafting the cold cathode technology. Korean Patent Laid-open No. 10-2009-098,458 discloses a system for generating terahertz electromagnetic waves. It is to be appreciated to those skilled in the art that the generating unit according to the preferred embodiment of the present invention can be changed or modified in various forms with reference to the technology of the terahertz wave generating system described in Korean Patent Laid-open No. 10-2009-098,458.

The detection unit 12 detects terahertz electromagnetic waves reflected from the tympanic cavity. In case that the reflected terahertz electromagnetic waves are a pulse type, the detection unit 12 detects a pulse signal using a photoconductive antenna or an electro-optic sampling method or includes a rotary optical delay line for a high-speed detection of the pulse signal. In case of detecting the continued-type terahertz electromagnetic waves, the detection unit 12 may use a schottky diode, a pyroelectric detector, a golay cell, or a bolometer or include a detector with a two-dimensional array structure, such as a microbolometer or a pyrocam. The detection unit 12 may detect a terahertz wave band radiated from the generating unit 11, and preferably, detect terahertz electromagnetic waves of 0.01 THz to 30 THz.

The camera 30 serves to provide image information so that a doctor can check the eardrum part with naked eyes in order to radiate terahertz electromagnetic waves toward the tympanic cavity located at the back of the eardrum. Therefore, the camera 13 takes a picture of the inner ear in order to acquire image information, and then, the acquired image information is transferred to the display unit 40 to display the image information or is displayed on another display unit, such that the doctor can check the position of the eardrum through a screen.

The otoscope 14 may be formed in a cone shape or a trumpet shape, and is inserted into an earhole in order to expand an earhole in a straight line such that the eardrum can be seen with naked eyes from the external auditory meatus.

Figure 2:
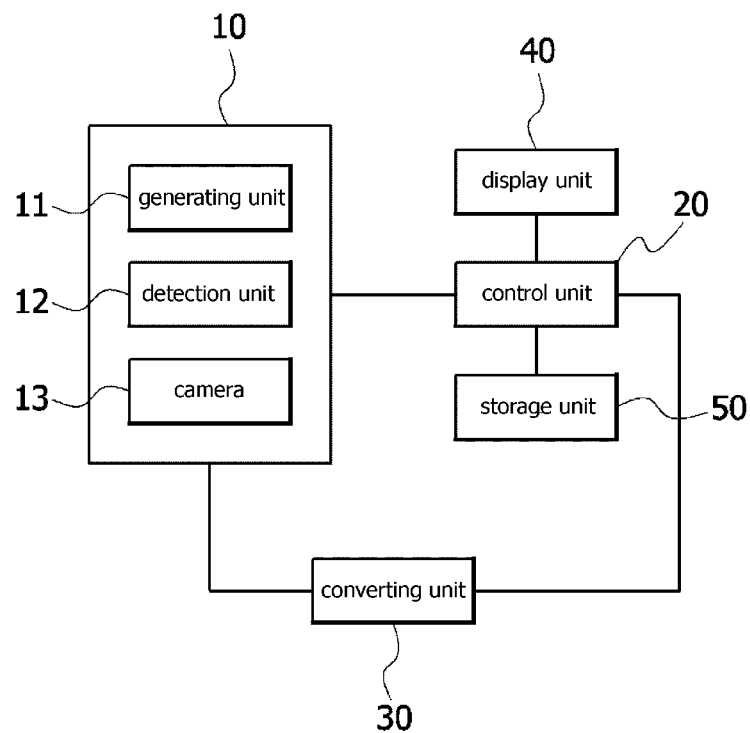
FIG. 2 is a block diagram of a system for diagnosing otitis media using terahertz electromagnetic waves according to a preferred embodiment of the present invention.

FIG. 2 is a block diagram of a system for diagnosing otitis media using terahertz electromagnetic waves according to a preferred embodiment of the present invention.

The system for diagnosing otitis media using terahertz electromagnetic waves according to the preferred embodiment of the present invention includes: a terahertz probe 10, a control unit 20 for checking occurrence of otitis media and discriminating kinds of otitis media using reflected terahertz electromagnetic waves; a converting unit 20 for converting the reflected terahertz electromagnetic waves into an electric signal; a display unit 40 for displaying an image generated from the control unit; and a storage unit 50 for storing the image generated from the control unit.

Description of the terahertz probe 10 will be omitted because it is the same as the above.

The converting unit 30 converts the reflected terahertz electromagnetic waves received from the detecting unit into an electric signal and transfers the electric signal to the control unit, and the control unit 20 analyzes the electric signal to check occurrence of otitis media and discriminate kinds of otitis media using reflected terahertz electromagnetic waves. Exudative otitis media generates inflammation due to an exudation gathered in the tympanic cavity, but suppurative otitis media generates inflammation due to suppurative secretion gathered in the tympanic cavity. Terahertz electromagnetic waves are easily absorbed because they are sensitive to moisture, and so, the control unit 20 analyzes strength of the reflected terahertz electromagnetic waves converted into the electric signal so as to judge whether the exudation or the suppurative secretion is gathered in the tympanic cavity, thus determining exudative otitis media or suppurative otitis media. Alternatively, the control unit 20 can check occurrence of otitis media and kinds of otitis media by analyzing a spectrum using the characteristic that the spectrum of the terahertz electromagnetic waves has different absorption rates and refractive rates according to biological tissues and moisture contents.

Moreover, the control unit 20 can generate an image using the electric signal transferred from the converting unit 30, and correctly diagnose occurrence, kinds, progression, and state of otitis media using the image.

Now, an example of a process of generating an image in the control unit 20 will be described. First, the converting unit 30 extracts and amplifies an amplitude signal and a phase signal from the reflected terahertz electromagnetic waves detected from the detection unit 12, divides the amplitude signal and a noise signal from noise, and then, transfers the signal to the control unit 20. The control unit 20 directly analyzes occurrence and kinds of otitis media using the amplitude signal and the phase signal received from the converting unit 30 or diagnoses by generating and analyzing an image. The diagnosis through the image is carried out through analysis of differences in brightness of cellular tissues or in color by temperature. The control unit 20 can make an image of the amplitude signal and an image of the phase signal or make an image simultaneously using the amplitude signal and the phase signal. The control unit 20 transfers the image to the display unit 40 and the storage unit 50. The display unit 40 can display the received image through various display means, and the storage unit 50 serves to store the received image using a memory device.

FIGS. 3 to 6 are graphs according to the preferred embodiment of the present invention.

FIGS. 3 to 6 show graphs made using an electric signal converted from reflected terahertz electromagnetic waves which are detected after being radiated to the skin of a biological tissue having characteristics the most similar to those of a human being's eardrum.

Figure 3:
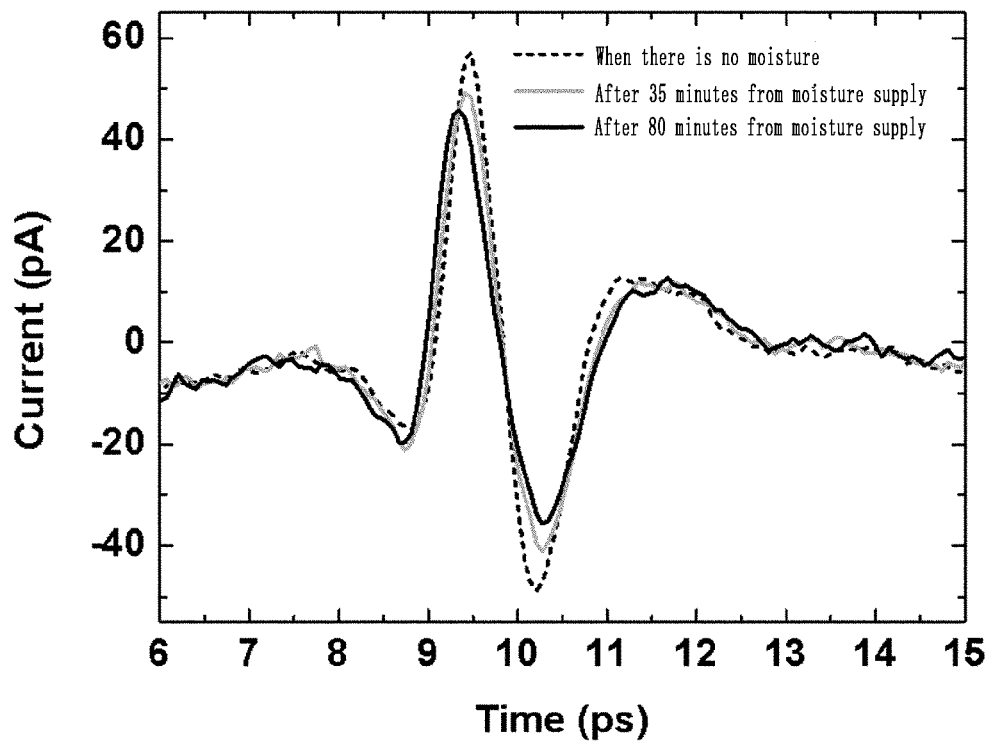
FIGS. 3 to 6 are graphs according to the preferred embodiment of the present invention.

Referring to FIG. 3, you can see that strength of the electric signal, namely, size of electric currents becomes smaller when moisture is gradually gathered in the tympanic cavity in comparison with the case that there is no moisture in the tympanic cavity (indicated by a dotted line in the drawing). It means that the control unit 20 can diagnose otitis media at the early stage by analyzing strength of the electric signal in the normal eardrum and strength of the electric signal in a patient's eardrum where the strength of the electric signal is gradually reduced when otitis media occurs.

Figure 4:
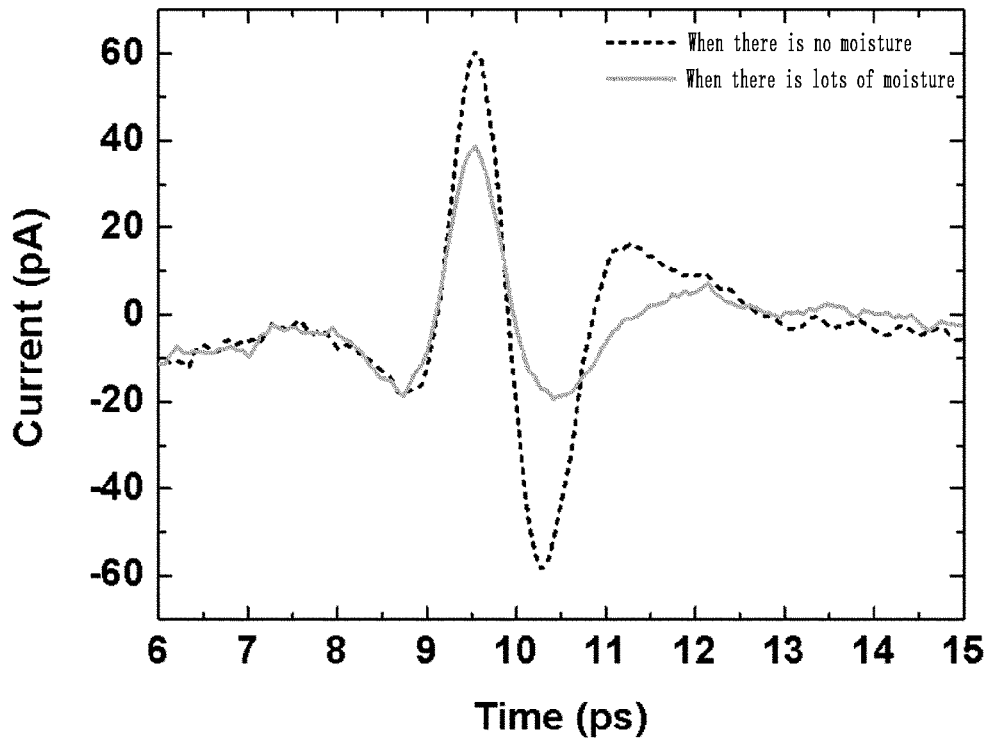

Next, referring to FIG. 4, in comparison with the case that there is no moisture in the tympanic cavity (indicated by a dotted line in the drawing), when lots of moisture is gathered in the tympanic cavity for a short period of time, strength of the electric signal becomes rapidly reduced. It means that the control unit 20 can diagnose the state and the degree of risk of otitis media by analyzing how much strength of the electric signal is reduced as time goes by.

Figure 5:
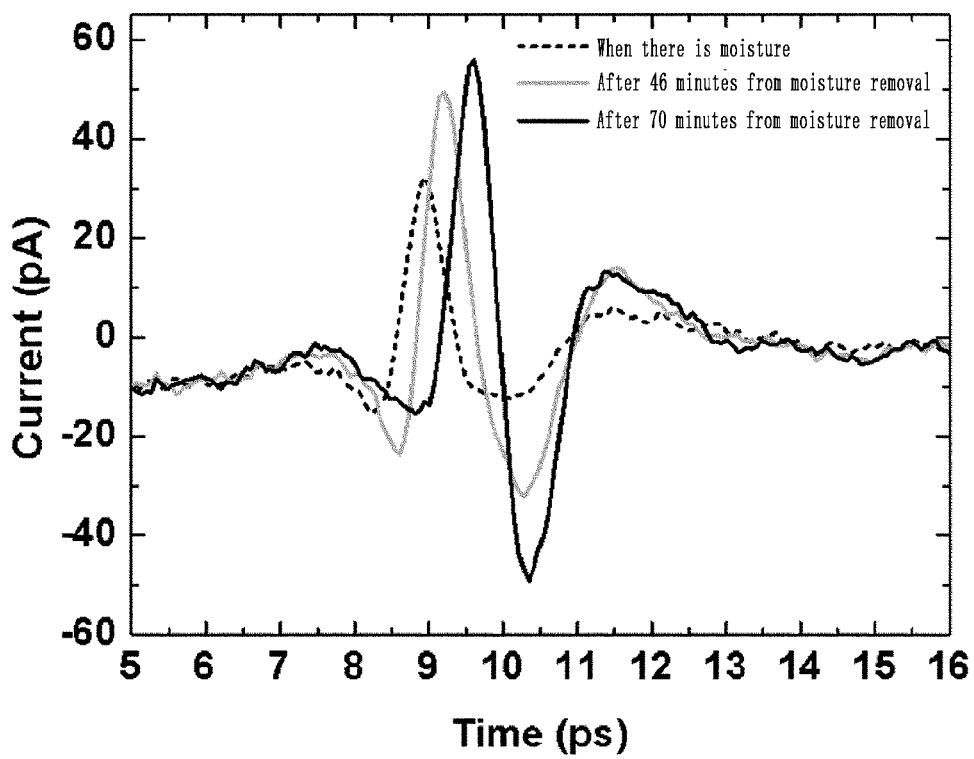

Next, referring to FIG. 5, in comparison with the case that there is moisture in the tympanic cavity (indicated by a dotted line in the drawing), when moisture is gradually removed from the tympanic cavity, strength of the electric signal is increased, and a phase is changed. It means that a point that a peak value of the electric signal is detected is changed because the form of the eardrum is changed according to the progression of otitis media. It also means that the control unit 20 can diagnose progressive otitis media and chronic otitis media using the strength of the electric signal and the point that the peak value of the electric signal is detected.

Figure 6:
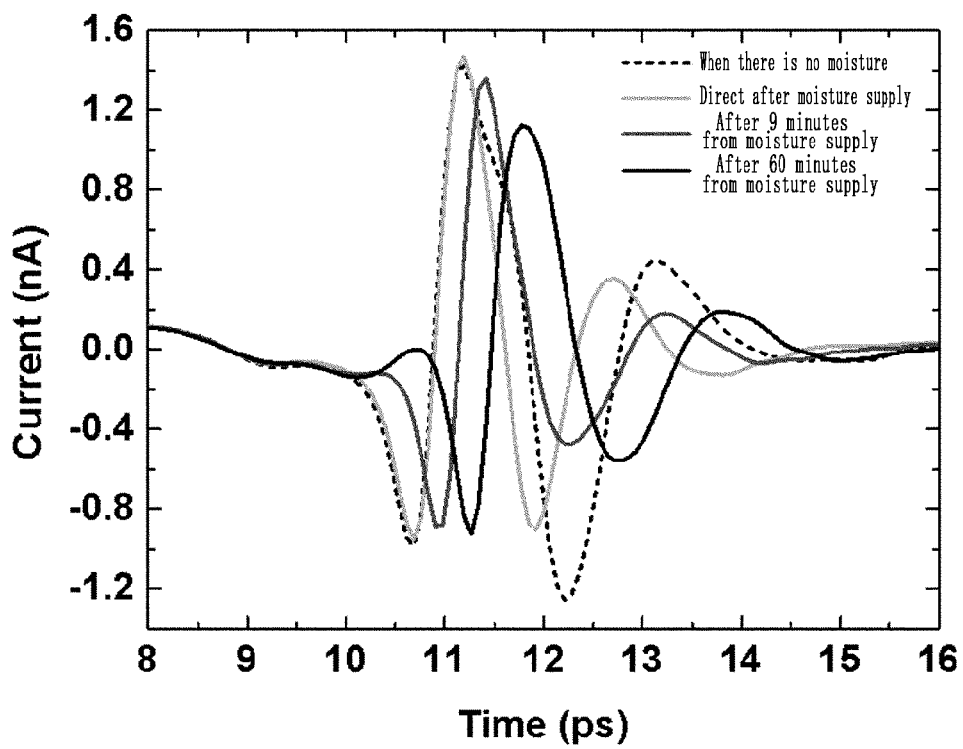

Next, referring to FIG. 6, in comparison with the case that there is no moisture in the tympanic cavity (indicated by a dotted line in the drawing), when moisture is gradually gathered in the eardrum, strength and phase of the electric signal are changed. Therefore, the control unit 20 can diagnose exudative otitis media by analyzing the strength of the electric signal, and diagnose acute otitis media and chronic otitis media by analyzing the state of the eardrum using strength and phase of the electric signal.

Figure 7:
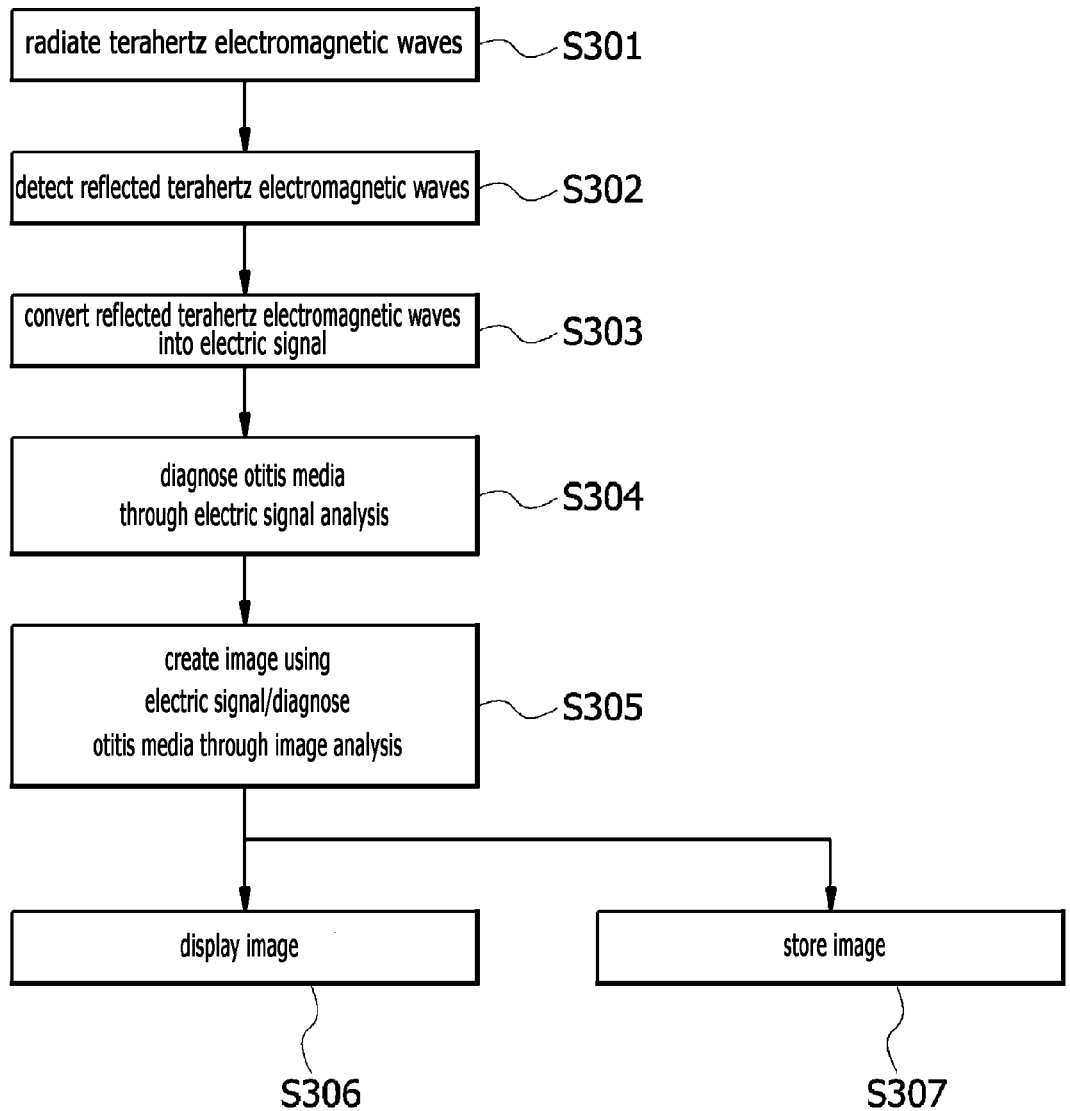
FIG. 7 is a flow chart showing a method for diagnosing otitis media using terahertz electromagnetic waves according to a preferred embodiment of the present invention.

FIG. 7 is a flow chart showing a method for diagnosing otitis media using terahertz electromagnetic waves according to a preferred embodiment of the present invention.

Terahertz electromagnetic waves are radiated toward the tympanic cavity from the generating unit 11 of the terahertz probe 10 inserted into the ear through the otoscope. In this instance, the doctor can check the position of the eardrum through image information of the inner ear acquired through the camera and control an exact radiation position. The radiated terahertz electromagnetic waves may be in the range of 0.01 THz to 30 THz, or may be ones of pulse type terahertz electromagnetic waves, continued-type terahertz electromagnetic waves, and semiconductor device type terahertz electromagnetic waves (S301).

The detection unit 12 detects reflected terahertz electromagnetic waves returned from the tympanic cavity after reaching the tympanic cavity through the eardrum. The detection unit 12 detects the reflected terahertz electromagnetic waves according to kinds of the terahertz electromagnetic waves radiated from the generating unit 11, namely, according to the pulse type terahertz electromagnetic waves, continued-type terahertz electromagnetic waves, and semiconductor device type terahertz electromagnetic waves. The detection unit 12 transfers the terahertz electromagnetic waves to the control unit 20 and the converting unit 30 (S302).

The converting unit 30 converts the received reflected terahertz electromagnetic waves into an electric signal. While converting the terahertz electromagnetic waves into the electric signal, the converting unit 30 amplifies the reflected terahertz electromagnetic waves and removes noise contained in the terahertz electromagnetic waves. The converting unit 30 transfers the electric signal converted from the reflected terahertz electromagnetic waves to the control unit 20 (S303).

The control unit 20 can determine occurrence and kinds of otitis media through the wavelength strength of the electric signal received from the converting unit or through the spectrum analysis (S304).

Furthermore, the control unit 20 may diagnose occurrence, progression, state and kinds of otitis media by creating and analyzing an image using the electric signal received from the converting unit 30 (S305).

The display unit 40 receives the image created from the control unit 20 and displays it using one of various display devices (S306).

The storage unit 50 receives the image created from the control unit 20, and stores it using one of various memory devices (S307).

In general, terahertz electromagnetic waves are frequencies in the range of 0.01 THz to 100 THz, but to use electromagnetic waves which have similar characteristics to the terahertz electromagnetic waves of the present invention even in frequency bands other than the above-mentioned frequency band belongs to the scope of the present invention. For instance, because electromagnetic waves having frequencies less than 300 THz in a middle infrared region are very similar in moisture absorption to terahertz electromagnetic waves, that the electromagnetic waves are used to diagnose otitis media does not depart from the scope of the present invention.

Unless otherwise defined herein, it will be understood that all words or terms used in the specification and claims should be interpreted as the meaning defined in commonly used dictionaries in the art. It will be further understood that the words or terms should be interpreted as having a meaning that is consistent with their meaning in the context of the relevant art and the technical idea of the invention, and should not be interpreted as excessively ideal or formal meaning unless otherwise defined.

What is claimed is:

1. A system for diagnosing otitis media using terahertz electromagnetic waves comprising:
a terahertz probe which includes a generating unit for radiating terahertz electromagnetic waves from the outside of an ear toward a tympanic cavity and a detection unit for detecting the reflected terahertz electromagnetic waves reflected from the tympanic cavity;

a converting unit which converts the reflected terahertz electromagnetic waves detected by the detection unit into an electrical signal and sends the electrical signal to a control unit; and a control unit which performs otitis media diagnosis using the electrical signal sent from the converting unit;

wherein the control unit diagnoses otitis media by discriminating occurrence, progression, and kinds of otitis media using at least one of strength and phase of the electric signal; and wherein the control unit diagnoses otitis media at the early stage by analyzing strength of the electric signal in the normal eardrum and strength of the electric signal in a patient's eardrum where the strength of the electric signal is gradually reduced when otitis media occurs, diagnoses the state and the degree of risk of otitis media by analyzing how much strength of the electric signal is reduced as time goes by, diagnoses progressive otitis media and chronic otitis media using the strength of the electric signal and the point at which the peak value of the electric signal is detected, diagnoses exudative otitis media by analyzing the strength of the electric signal, and diagnoses acute otitis media and chronic otitis media by analyzing the state of the eardrum using strength and phase of the electric signal.

2. The otitis media diagnosing system according to claim 1, wherein the generating unit radiates terahertz electromagnetic waves ranging from 0.01 THz to 30 THz.

3. The otitis media diagnosing system according to claim 1, wherein the generating unit radiates at least ones of pulse type terahertz electromagnetic waves, continued-type terahertz electromagnetic waves, and semiconductor device type terahertz electromagnetic waves.

4. The otitis media diagnosing system according to claim 1, wherein the generating unit comprises:
a generating part for generating terahertz electromagnetic waves;
a transferring part for transferring the generated terahertz electromagnetic waves to the otoscope; and
a radiating part for radiating the transferred terahertz electromagnetic waves to the tympanic cavity.

5. The otitis media diagnosing system according to claim 1, wherein the control unit generates an image using the electric signal.

6. The otitis media diagnosing system according to claim 5, wherein the control unit diagnoses otitis media by analyzing the image generated using the electric signal.

7. The otitis media diagnosing system according to claim 5, further comprising:
a display unit for displaying the image generated from the control unit.

8. The otitis media diagnosing system according to claim 5, further comprising:
a storage unit for storing the image generated from the control unit.

9. The otitis media diagnosing system according to claim 1, wherein the converting unit amplifies a signal of the reflected terahertz electromagnetic waves and removes noise contained in the reflected terahertz electromagnetic waves.

10. The otitis media diagnosing system according to claim 1, wherein the terahertz probe further comprises a camera for acquiring image information of the inner ear.

11. The otitis media diagnosing system according to claim 1, wherein the terahertz probe further comprises an otoscope which is inserted into the inner ear.

* * * * *